United States Patent [19]
Hedberg et al.

[11] Patent Number: 5,662,687
[45] Date of Patent: Sep. 2, 1997

[54] IMPLANTABLE HEART DEFIBRILLATOR

[75] Inventors: Sven-Erik Hedberg, Kungsaengen; Martin Obel, Danderyd; Kurt Hoegnelid, Villavägen, all of Sweden

[73] Assignee: Pacesetter AB, Solna, Sweden

[21] Appl. No.: 407,046

[22] Filed: Mar. 17, 1995

Related U.S. Application Data

[63] Continuation-in-part of Ser. No. 114,344, Sep. 1, 1993, abandoned.

[30] Foreign Application Priority Data

Sep. 16, 1992 [SE] Sweden .................................. 9202664

[51] Int. Cl.⁶ .................................................. A61N 1/39
[52] U.S. Cl. ................................................................ 607/5
[58] Field of Search ........................................... 607/5, 7

[56] References Cited

U.S. PATENT DOCUMENTS

| | | | |
|---|---|---|---|
| 4,354,497 | 10/1982 | Kahn | 607/5 |
| 4,403,614 | 9/1983 | Engle et al. | 607/5 |
| 4,800,883 | 1/1989 | Winstrom | 607/7 |
| 4,821,723 | 4/1989 | Baker, Jr. et al. | 607/7 |
| 4,996,984 | 3/1991 | Sweeney | 607/5 |
| 5,235,978 | 8/1993 | Hirschberg et al. | 607/5 |
| 5,385,576 | 1/1995 | Noren et al. | |

FOREIGN PATENT DOCUMENTS 0326290  8/1989  European Pat. Off. ............ 607/5

OTHER PUBLICATIONS

"Implantable Cardioverters and Defibrillators," Troup, Current Problems in Cardiology, O'Rourke, Ed., vol. XIV, No. 12, Dec. 1989.

Primary Examiner—William E. Kamm
Attorney, Agent, or Firm—Hill, Steadman & Simpson

[57] ABSTRACT

An implantable heart defibrillator includes a pulse generator controlled by a control unit for emitting defibrillation pulses. The pulse generator is controllable to emit a number of low-energy defibrillation pulses, having a lower pulse amplitude and a shorter pulse duration than a conventional defibrillation pulse, with the total energy in the number of low-energy defibrillation pulses being less than the energy in a conventional defibrillation pulse. Each pulse in the number of low-energy defibrillation pulses, however, contains enough energy to depolarize heart cells oriented favorably in relation to the direction of the electrical field of the low-energy defibrillation pulse.

20 Claims, 4 Drawing Sheets

IMPLANTABLE HEART DEFIBRILLATOR

This is a continuation-in-part of application Ser. No. 08/114,344, filed Sep. 1, 1993, now abandoned.

BACKGROUND OF THE INVENTION

1. Field of the Invention

The present invention is directed to an implantable heart defibrillator of the type having a pulse generator, controlled by a control unit, for emitting defibrillation pulses.

2. Description of the Prior Art

Due to a high intracellular concentration of potassium, a heart tissue cell "at rest" is in a polarized condition, i.e., its interior is more negative than its exterior. When stimulated (excited) by the presence of an electrical field, the cell depolarizes so that its interior is momentarily more positive than its exterior. When the electrical field is removed, the cell requires a certain amount of time to repolarize. When the cell is in this condition, it is said to be refractory. A refractory cell will not respond to a renewed stimulation. Both healthy and pathological depolarization waves are conducted in a heart by the successive depolarization and repolarization of cells along a propagation path. A stimulated cell, in turn, causes neighboring cells to be similarly stimulated, thereby propagating the depolarization wave.

If the heart's natural pacemaker is unable to initiate such depolarization waves, it can be artificially assisted by pacemaker-generated stimulation pulses. The reverse situation applies in the case of fibrillation, i.e., the disorganized generation of depolarization waves within the heart. For fibrillation therapy, i.e. defibrillation, the goal is to prevent the propagation of the disorganized depolarization waves. This is accomplished in conventional defibrillation by applying a sufficiently strong electric field to the entire heart, or substantial portions thereof, so as to make as many heart cells as possible refractory for an unnaturally long time. Since the refractory cells are incapable of being stimulated, this prevents the disorganized depolarization waves from being further propagated, and the heart's natural pacemaker, or an artificial pacemaker, thereafter regains control of the generation of the depolarization waves.

It is known that the heart cells are anisotropic, i.e., an electrical field, such as that generated by a defibrillation pulse, will stimulate a heart tissue cell more readily if the cell has a given (preferred) orientation in relation to the defibrillating electrical field. The electrical field strength required to stimulate a heart tissue cell can vary between two orthogonal directions by a factor of 2 to 5. Therefore, any specified area of heart tissue will contain a collection of differently oriented cells, some of which will be susceptible to stimulation with a lower magnitude electrical field, while others will require a higher magnitude field in order to be stimulated. In conventional defibrillating techniques, the defibrillation pulse which is generated is of such a high magnitude as to ensure that all tissue cells, regardless of their orientation, will be stimulated (depolarized). This requires the generation of a defibrillation pulse at a voltage on the order of 500 to 1000 volts, and having an energy content of 10 joules or more.

A cardioversion system is disclosed in German OS 3715822 wherein the cardioversion pulse is chopped into a sequence of brief pulses in order to save energy. A normal, single cardioversion pulse will have an exponentially decaying waveform or envelope. The general waveform or envelope of the pulse "package" consisting of the sequence of brief pulses in this known system still displays the conventional exponentially decaying configuration, i.e., the amplitude of the individual pulses in the pulse package produced by chopping is the same as that of a conventional cardioversion pulse.

SUMMARY OF THE INVENTION

It is an object of the present invention to utilize the above-described anisotropy of the heart tissue cells to achieve cardiac defibrillation with lower energy than has heretofore been possible.

The above object is achieved in an implantable heart defibrillator having a pulse generator controlled by a control unit for emitting defibrillation pulses, the pulse generator being controllable to emit a plurality of low-energy defibrillation pulses. As used herein, the term "low-energy defibrillation pulse" means a pulse having a lower pulse amplitude and a shorter pulse duration than a conventional defibrillation pulse. The total energy in the plurality of low-energy defibrillation pulses is less than the energy contained in a conventional defibrillation pulse, but each low-energy defibrillation pulse contains enough energy to depolarize those heart tissue cells which are favorably oriented in relation to the direction of the electrical field associated with the low-energy defibrillation pulse. Consistent with the earlier discussion, a "favorably oriented" tissue cell, as used herein, means a tissue cell oriented so as to be depolarizable by the aforementioned low-energy pulse.

Thus, the defibillator according to the invention emits a plurality of low-energy defibrillation pulses respectively having energies which are insufficient to defibrillate the entire heart, but which depolarize most non-refractory heart tissue cells having a given orientation in relation to the electrical field associated with the low-energy pulse. Since the heart tissue cells are capable of exciting neighboring cells for a rather long period of time, the aim is to prevent neighboring cells from being stimulated as they leave their refractory phase, and to thereby prevent propagation of the signal. Even if it is not possible to prevent neighboring cells from becoming stimulated, it is possible with the invention to cause the neighboring cells to be exalted only with a low-energy defibrillation pulse, and by the emission of a plurality of such pulses, to prevent cells leaving their refractory phase from becoming re-excited. The emission of a plurality of relatively low-energy pulses, whose energy is still sufficient to depolarize heart tissue cells oriented in the most favorable direction, during different phases of the propagation of a depolarization wave thereby stops the propagation of such a wave at any given moment in the aforementioned favorably direction.

Thus, heart defibrillation is achieved by using a plurality of low-energy defibrillation pulses, whose total energy is less than the energy in a conventional defibrillation shock or pulse.

In one embodiment of the defibrillator of the invention, the pulse generator emits defibrillation pulses with a lower pulse amplitude and shorter pulse duration, with each pulse consisting of a burst of impulses. This prolongs the refractory period of certain heart tissue cells, so that an increasing number of heart tissue cells become refractory, and the prospects for terminating fibrillation increase.

DESCRIPTION OF THE PREFERRED EMBODIMENTS

Figure 1:
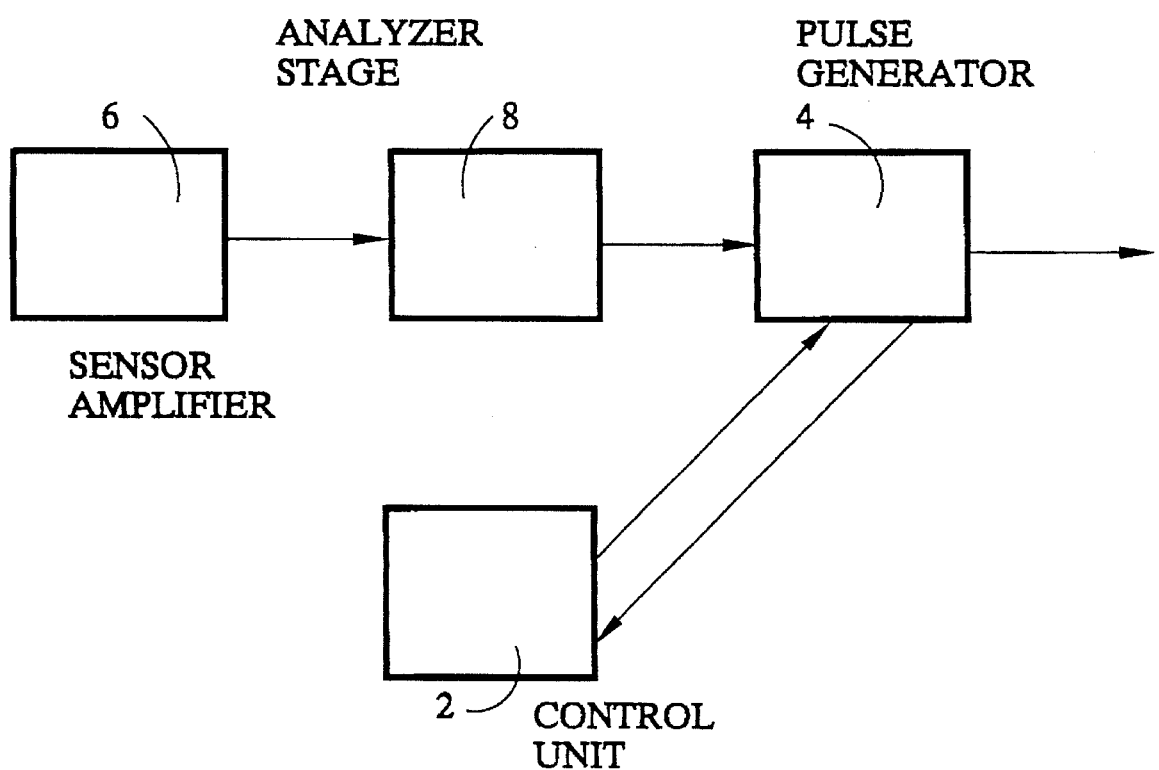
FIG. 1 is a schematic block diagram of a cardiac defibrillator constructed in accordance with the principles of the present invention.

The defibrillator shown in FIG. 1 includes a sensor having an associated sensor amplifier 6 for sensing and amplifying electrical signals obtained from the heart. The amplified sensor signal is analyzed in an analyzer stage 8 to ascertain whether cardiac fibrillation is present. This is accomplished in a known manner.

The results of the analysis are supplied to a control unit 2 which, if fibrillation is detected, commands a pulse generator 4 to deliver a plurality of defibrillation pulses to the heart. These defibrillation pulses may include one or more conventional defibrillation pulses, as well as low-energy defibrillation pulses having a lower pulse amplitude and shorter pulse duration than the conventional defibrillation pulse. These pulses are supplied to the heart and the defibrillation electrodes (not shown).

The pulse generator 4 includes an output stage (not separately shown) which contains switches controlled by a microprocessor contained in the control unit 2, so that pulse sequences having selectable pulse configurations are emitted.

The pulse amplitude and the pulse width, as well as the intervals between pulses, can be set as desired by programming the microprocessor in the control unit 2.

The defibrillator according to the invention can emit monophasic or biphasic defibrillation pulses, or combinations of monophasic and biphasic defibrillation pulses.

Figure 2A:
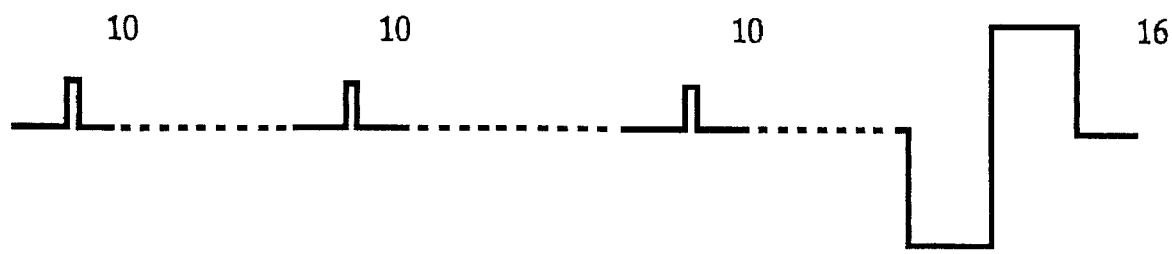
FIGS. 2a, 2b, 2c and 3 respectively show examples of sequences of low-energy defibrillation pulses, followed in each case by a convention defibrillation pulse, which are achievable using the defibrillator according to the invention shown in FIG. 1.
Figure 2B:
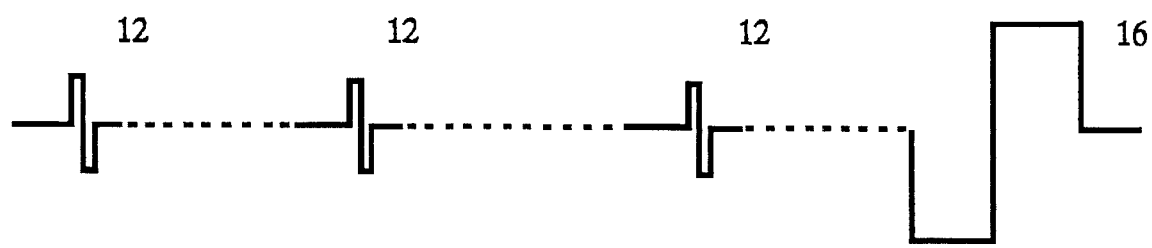
Figure 2C:
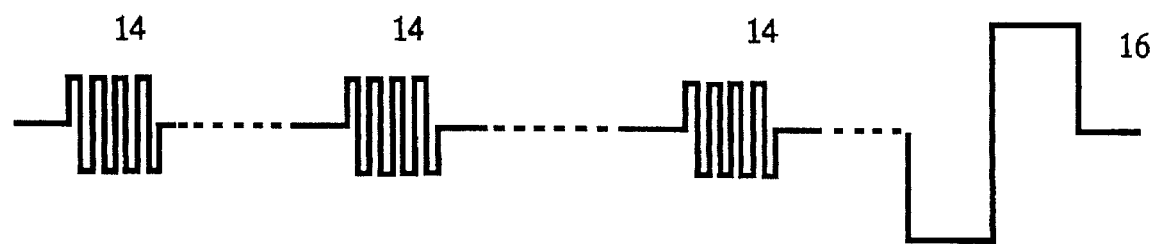

Three examples of sequences of low-energy defibrillation pulses 10, 12, 14 are respectively shown in FIGS. 2a, 2b and 2c, following in each case by a conventional defibrillation pulse 16. As can be seen by these examples, the low-energy defibrillation pulses 10, 12 and 14 have considerably lower amplitude and shorter pulse duration than the conventional defibrillation pulse 16.

The pulse generator 4 includes a power source and a high-voltage generator, including one or more chargeable capacitors, for emitting conventional defibrillation pulses at a voltage on the order of magnitude of 500–1,000 volts and an energy content of 10 to 40 joules. In the defibrillator according to the invention, the switches of the output stage are operated to control charging and discharging of the capacitors so that effective heart defibrillation can be achieved solely with the low-energy defibrillation pulses 10, 12 and 14.

The first sequence of low-energy defibrillation pulses shown in FIG. 2a comprises monophasic pulses 10. The pulse sequences shown in FIGS. 2b and 2c respectively consist of biphasic pulses 12 and 14. The pulse sequence 14 of FIG. 2c, in addition to being biphasic, consists of low-energy defibrillation pulses arranged in separate groups.

The total energy of the low-energy defibrillation pulses in each of the examples of FIGS. 2a, 2b and 2c is less than the energy in a conventional defibrillation pulse 16.

The interval between the low-energy defibrillation pulses 10, 12 and 14 in the respective examples can vary from about 1 millisecond to about 100 milliseconds, and is preferably on the order of 10 milliseconds.

The groups of low-energy defibrillation pulses can include 2 to 10 pulses.

The low-energy defibrillation pulses can be emitted for a period from about 10 milliseconds up to approximately the duration of one refractory period, or slightly longer. If a conventional defibrillation pulse 16 is emitted following the low-energy defibrillation pulses, the time for the emission of the conventional defibrillation pulse can be selected from 0 seconds, i.e. the conventional defibrillation pulse 16 is emitted immediately after the last low-energy defibrillation pulse 10, 12 or 14, up to several seconds after the last low-energy defibrillation pulse.

Figure 3:
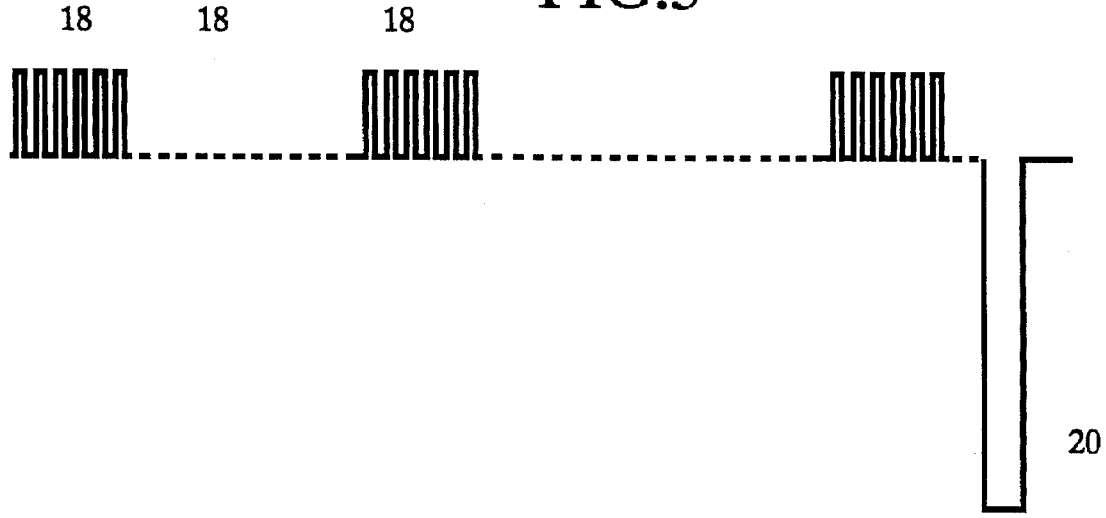

A further embodiment of the invention is illustrated in FIG. 3 wherein each low-energy defibrillation pulse consists of a burst of impulses 18. The burst of impulses 18 is generated by appropriate operation of the switches of the output stage 4. In this manner, the refractory time of certain cells can be prolonged, making more heart tissue cells refractory and thereby increasing the likelihood of terminating the fibrillation. In the example shown in FIG. 3, the low-energy fibrillation pulses formed by the impulses 18 are followed by a conventional defibrillation pulse 20. As noted above, in many instances defibrillation can be achieved solely by the low-energy defibrillation pulses themselves, in which case the energy of the conventional defibrillation pulse 16 or 20 is saved. The specific configuration of the low-energy pulses is unimportant to the functioning of the defibrillator according to the invention, and can easily be varied in many ways.

Figure 4:
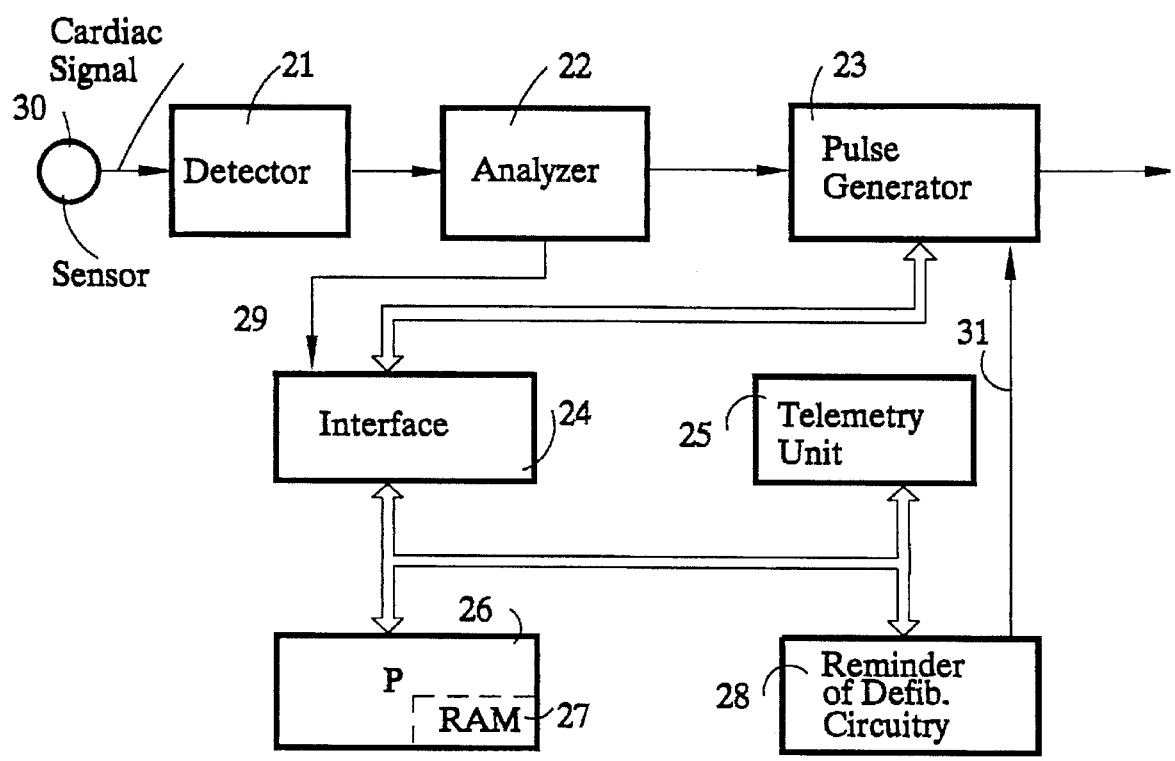
FIG. 4 is a schematic block diagram of a cardiac defibrillator constructed in accordance with the principles of the present invention, showing further details for the production of the pulses shown in FIGS. 2a, 2b, 2c and 3.

The defibrillation pulse sequences shown in each of FIGS. 2a, 2b, 2c and 3 can be produced by circuitry schematically shown in FIG. 4. A signal indicative of cardiac activity, such as in the form of an ECG signal, is supplied from a sensor implanted in or around the heart to a detector 21, which may include suitable signal editing circuitry. The output of the detector 21 is supplied to an analyzer 22, which may be of any type well-known to those skilled in the art for analyzing the waveform from the detector 21 to determine the presence of ventricular fibrillation, such as is disclosed in U.S. Pat. No. 5,385,576, the teachings of which are incorporated herein by reference. When the presence of ventricular fibrillation is identified, the analyzer 22 supplies a signal on line 29 to an interface 24. The interface 24 has a data bus connection to a pulse generator 23 as well as to a microprocessor (μP) 26. The pulse generator 23 contains an arrangement of capacitors which are charged and discharged at appropriate amplitudes and times by switches under the control of a program stored in a RAM 27 in the microprocessor 26. The switches are selectively opened and closed to charge the capacitors in the pulse generator 23 to produce one of the pulse sequences shown in FIGS. 2a, 2b, 2c or 3.

The remainder of the defibrillation circuitry 28 (such as a battery, battery level monitoring circuitry, further logic circuits, etc.) are also in communication via a data bus with the microprocessor 26, and charging voltage is supplied to the pulse generator 23 via line 31. The microprocessor 26 can be reprogrammed, and different data can be entered into the RAM 27, by means of a telemetry unit 25, which is also connected via a data bus to the microprocessor 26, as well as being connected to the remainder of defibrillation circuitry 28. The telemetry unit 25 communicates with an extracorporeal programmer (not shown) in a known manner.

Figure 5:
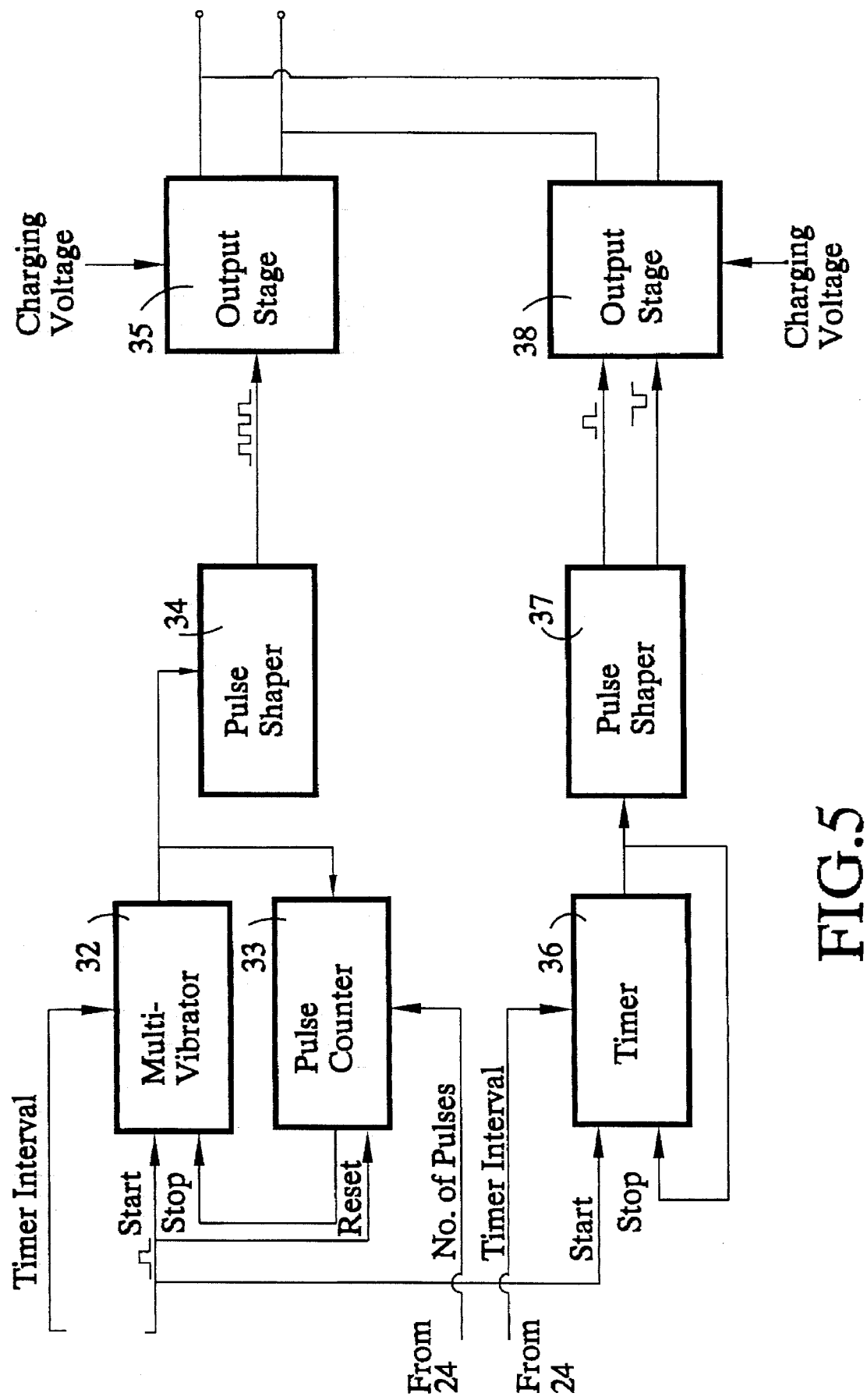
FIG. 5 is a schematic block diagram of a preferred embodiment of a pulse generator for use in the defibrillator of the invention.

A schematic illustration of a preferred embodiment of a pulse generator, which can serve as the pulse generator 23, is shown in FIG. 5. The upper portion thereof generates the low-energy pulses, and the lower portion thereof generates the conventional defibrillation pulse (if such a conventional pulse is necessary).

For generating the low-energy pulses, signals according to the operating program are received from the microprocessor 26 via the interface 24. These signals indicate the number of low-energy pulses to be generated, their duration, and the interval between pulses. An initialization pulse is supplied to a multivibrator 32 as well as to the reset input of a pulse counter 33. This causes the multivibrator to begin emitting a train of output pulses, which are also supplied to a count input of the pulse counter 33. When the appropriate number of pulses have been emitted by the multivibrator, as counted by the pulse counter 33, the pulse counter emits a stop signal to the multivibrator 32. The pulses emitted by the multivibrator 32 are supplied to a pulse shaper 34 which, in a known manner, edits the pulses so as to be in a suitable form for supply to an output stage 35. If biphasic low-energy pulses are to be produced, as in the example shown in FIG. 2b, the pulse shaper 34 can be hard-wired to produce such a biphasic waveform from each incoming pulse from the multivibrator. For greater flexibility, the pulse shaper 34 can include a dedicated circuit for that purpose, which can be switched into and out of the normal signal path by a signal from the microprocessor 26 on a separate line (not shown), so that monophasic or biphasic pulses can be selectively produced.

The output stage 35 is supplied with a charging voltage from the power source. This charging voltage is supplied via line 31 from the remainder of defibrillation circuitry 28. The output stage 35 contains capacitors which are charged by this charging voltage dependent on the pulse train supplied thereto by the pulse shaper 34, so as to produce any one of the low-energy pulse sequences shown in FIGS. 2a, 2b, 2c or 3.

For producing the conventional pulses, a timer 36 begins measuring a time starting from the receipt of the initialization pulse by the multivibrator 32. This time will be of a duration which is longer than the entire sequence of low-energy pulses. When this time has elapsed, the timer 36 supplies an output signal, which also causes the timer to stop, to the pulse shaper 37, which supplies an input control pulse to an output stage 38. As an alternative to the above-described operation of the pulse shaper 34, the pulse shaper 37 is shown as having two output lines on which a positive pulse and a negative pulse respectively appear, for producing a biphasic conventional pulse, if desired. It will be understood that the pulse shaper 34 may operate in the manner described for the pulse shaper 37, or vice versa. The output stage 38 is also supplied with a charging voltage via line 31. The low-energy pulse sequence followed by the conventional pulse is supplied to a patient via output electrodes connected to both output stages 35 and 38.

Although modifications and changes may be suggested by those skilled in the art, it is the intention of the inventor to embody within the patent warranted hereon all changes and modifications as reasonably and properly come within the scope of the his contribution to the art.

We claim as our invention:

1. An implantable cardiac defibrillator comprising:

pulse generator means for delivering pulses in vivo to a heart; and control means for operating said pulse generator for emitting, within one refractory period of said heart, a plurality of low-energy pulses respectively having an electrical field associated therewith and an energy insufficient to defibrillate said heart and said pulses in combination having a total energy which is less than a defibrillation energy which is capable of defibrillating the entirety of said heart, and said energy of each low-energy pulse being in a range of 2 to 5 times less than said defibrillation energy for giving each low-energy pulse sufficient energy for depolarizing heart tissue cells oriented in a favorable direction in relation to the electrical field associated with the low-energy pulse.

2. A defibrillator as claimed in claim 1 wherein said control means comprises means for operating said pulse generator means for emitting said low-energy pulses at intervals in a range from about 1 millisecond to about 100 milliseconds.

3. A defibrillator as claimed in claim 1 wherein said control means comprises means for operating said pulse generator means for emitting said low-energy pulses at intervals of approximately 10 milliseconds.

4. A defibrillator as claimed in claim 1 wherein said control means comprises means for operating said pulse generator means for emitting said low-energy pulses in sequence containing 2 to 10 low-energy pulses.

5. A defibrillator as claimed in claim 1 wherein said control means comprises means for operating said pulse generator means for emitting monophasic low-energy pulses.

6. A defibrillator as claimed in claim 1 wherein said control means comprises means for operating said pulse generator means for emitting biphasic low-energy pulses.

7. A defibrillator as claimed in claim 1 wherein said control means comprises means for operating said pulse generator means for emitting a combination of monophasic and biphasic low-energy pulses.

8. A defibrillator as claimed in claim 1 wherein said control means comprises means for operating said pulse generator means for emitting low-energy pulses each consisting of a burst of impulses.

9. A defibrillator as claimed in claim 1 wherein said control means comprises means for operating said pulse generator means for emitting a single defibrillation pulse having said defibrillation energy after said low-energy pulses.

10. A defibrillator as claimed in claim 9 wherein said control means comprises means for operating said pulse generator means for emitting said single defibrillation pulse within zero to several seconds after a last of said low-energy pulses.

11. A method for defibrillating a heart comprising the steps of:

generating a plurality of low-energy pulses within one refractory period of said heart, each low-energy pulse having an electrical field associated therewith and an energy which is insufficient to defibrillate said heart, and said low-energy pulses in combination having a total energy which is less than a defibrillation energy which is capable of defibrillating the entirety of said heart, and each low-energy pulse having an energy which is in a range of 2 to 5 times less than said defibrillation energy for giving said low-energy pulses sufficient energy for depolarizing heart tissue cells which are favorably oriented relative to the direction of the electrical field associated with the low-energy pulse; and delivering said low-energy pulses in vivo to a heart to terminate fibrillation of said heart.

12. A method as claimed in claim 11 wherein the step of generating said low-energy pulses is further defined by generating said low-energy pulses at intervals in a range of about 1 millisecond to about 100 milliseconds.

13. A method as claimed in claim 11 wherein the step of generating said low-energy pulses is further defined by generating said low-energy pulses at intervals of approximately 10 milliseconds.

14. A method as claimed in claim 11 wherein the step of generating said low-energy pulses is further defined by generating said low-energy pulses in sequences containing 2 to 10 low-energy defibrillation pulses.

15. A method as claimed in claim 11 wherein the step of generating said low-energy pulses is further defined by generating monophasic low-energy pulses.

16. A method as claimed in claim 11 wherein the step of generating said low-energy pulses is further defined by generating biphasic low-energy pulses.

17. A method as claimed in claim 11 wherein the step of generating said low-energy pulses is further defined by generating a combination of monophasic and biphasic pulses.

18. A method as claimed in claim 11 wherein the step of generating said low-energy pulses is further defined by generating a burst of impulses comprising each low-energy pulse.

19. A method as claimed in claim 11 comprising the additional step of:

generating and delivering a single pulse having said defibrillation energy after said low-energy pulses.

20. A method as claimed in claim 19 wherein the step of generating and delivering said single defibrillation pulse is further defined by delivering a single defibrillation pulse within a period of time from zero to several second after a last low-energy pulse.

* * * * *